United States Patent
Fukuhara et al.

(10) Patent No.: US 9,841,268 B2
(45) Date of Patent: Dec. 12, 2017

(54) IMAGING APPARATUS

(71) Applicant: CANON KABUSHIKI KAISHA, Tokyo (JP)

(72) Inventors: Makoto Fukuhara, Yokohama (JP); Nobuhiro Tomatsu, Yokohama (JP); Toshiharu Sumiya, Kawasaki (JP); Makoto Sato, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 96 days.

(21) Appl. No.: 14/742,372

(22) Filed: Jun. 17, 2015

(65) Prior Publication Data
US 2015/0369586 A1   Dec. 24, 2015

(30) Foreign Application Priority Data

Jun. 18, 2014   (JP) .................................. 2014-125733

(51) Int. Cl.
*G01B 9/02* (2006.01)
*A61B 3/10* (2006.01)
*A61B 5/00* (2006.01)

(52) U.S. Cl.
CPC .......... *G01B 9/02011* (2013.01); *A61B 3/102* (2013.01); *A61B 5/0066* (2013.01); *G01B 9/02058* (2013.01); *G01B 9/02091* (2013.01); *G01B 2290/70* (2013.01)

(58) Field of Classification Search
None
See application file for complete search history.

(56) References Cited

U.S. PATENT DOCUMENTS

| 7,723,670 B1 | 5/2010 | Yan | |
| 8,004,749 B1* | 8/2011 | Hsieh | G02F 2/00 356/477 |
| 2005/0228292 A1 | 10/2005 | DiMarzio | |
| 2010/0067020 A1 | 3/2010 | Podoleanu | |
| 2011/0221857 A1* | 9/2011 | Tatsuno | B41J 2/471 347/259 |

FOREIGN PATENT DOCUMENTS

| CN | 103211572 A | 7/2013 |
| EP | 0513970 A2 | 11/1992 |
| EP | 1162491 A2 | 12/2001 |
| JP | 2008272256 A | 11/2008 |

OTHER PUBLICATIONS

J. Biomed. Opt. 18(2), 026008 (Feb. 1, 2013), Teresa Torzichy et al. "Retinal polarization-sensitive optical coherence tomography at 1060 nm with 350 kHz A-scan rate using a Fourier domain mode locked laser".

* cited by examiner

*Primary Examiner* — Shawn Decenzo
(74) *Attorney, Agent, or Firm* — Canon USA Inc., IP Division

(57) ABSTRACT

An imaging apparatus configured to image an object to be examined is provided. The apparatus includes a splitting unit configured to split light obtained by combining the returned light and the reference light into a plurality of lights having different polarization components; and a detecting unit configured to detect the plurality of lights. The apparatus further includes a correcting unit configured to correct a phase difference between different polarization components generated by an optical member provided on an optical path of the measurement light or an optical path of the reference light.

10 Claims, 7 Drawing Sheets

IMAGING APPARATUS

BACKGROUND OF THE INVENTION

Field of the Invention

This disclosure relates to an imaging apparatus configured to image an object to be examined by detecting a plurality of lights having different polarization components.

Description of the Related Art

In recent years, a tomographic image pickup using an interference by low coherence light (Optical Coherence Tomography: OCT) apparatus (hereinafter, referred to as OCT apparatus) has been put into practical use. With an OCT apparatus, a tomographic image of an object to be examined can be obtained at a high resolution and in a non-invasive manner. Therefore, the OCT apparatus is becoming an absolutely imperative apparatus for obtaining the tomographic image of an eyeground (fundus) of an eye to be examined specifically in ophthalmic field. In fields other than ophthalmology, an attempt is being made to take tomographic images of wall surfaces of a digestive organ, and a circulatory organ, by configuring the OCT apparatus to perform a tomographic observation of the skin, or as an endoscope or catheter.

In an ophthalmology OCT apparatus, an attempt is made to acquire not only a normal OCT image (also referred to as a luminance image) that represents the shape of the eyeground tissue, but also a function OCT image that represents optical characteristics and movements of the eyeground tissue. In particular, a polarization-sensitive OCT apparatus is developed as one of a function OCT apparatus, and is configured to acquire a signal by using a polarization parameter of light. The polarization-sensitive OCT apparatus is capable of drawing a nerve fiber layer having a birefringent property and a retina layer having a property of resolving polarization, so that research aiming at glaucoma or age-related macular degeneration is being advanced.

At this time, the polarization-sensitive OCT apparatus forms a polarization OCT image by using the polarization parameter (retardation and orientation), which is one of the optical characteristics of the eyeground tissue, so that discrimination and segmentation of the eyeground tissue are performed. Generally, the polarization-sensitive OCT apparatus includes an optical system which is capable of correcting the polarized state of a measurement light and a reference light of the OCT apparatus by using a wavelength plate (for example, ¼ wavelength plate or a ½ wavelength plate). The polarized state of light ejected from a light source is corrected into a desired polarized state. The polarized state of a measurement light with which a sample is irradiated into a desired polarized state, the polarized state of the measurement light with which the sample is irradiated is corrected into a desired polarized state, and the light corrected in polarization is used to split and detect the interference light thereof as two orthogonal linearly-polarized beams, whereby a polarization OCT image is generated (J. Biomed. Opt. 18(2), 026008 (Feb. 1, 2013), Teresa Torzichy et al. "Retinal polarization-sensitive optical coherence tomography at 1060 nm with 350 kHz A-scan rate using a Fourier domain mode locked laser").

SUMMARY OF THE INVENTION

This disclosure provides an imaging apparatus according to an aspect configured to image an object to be examined including: a splitting unit configured to split light obtained by combining a returned light from an object to be examined irradiated with a measurement light and a reference light corresponding to the measurement light into a plurality of lights having different polarization components; and a detecting unit configured to detect the plurality of lights, wherein a correcting unit configured to correct a phase difference between different polarization components generated by an optical member provided on an optical path of the measurement light or an optical path of the reference light.

This disclosure also provides an imaging apparatus according to another aspect including: a splitting unit configured to split the returned light from the object to be examined irradiated with the measurement light into a plurality of lights having different polarization components; and a detecting unit configured to detect the plurality of lights, wherein a correcting device configured to correct a phase difference between different polarization components generated by an optical member provided on an optical path.

Further features of the present invention will become apparent from the following description of embodiments with reference to the attached drawings. Each of the embodiments of the present invention described below can be implemented solely or as a combination of a plurality of the embodiments or features thereof where necessary or where the combination of elements or features from individual embodiments in a single embodiment is beneficial.

DESCRIPTION OF THE EMBODIMENTS

In order to reduce the size of an apparatus for example, a configuration in which an optical path is bent by using a reflecting member such as a mirror is generally used. At this time, a property that a phase difference among different polarization components of light reflected from a reflecting surface (phase delay) is generated depending on a dielectric constant (complex index of refraction) of the reflecting surface of a mirror or the like is generally known. Therefore, the phase difference is generated by the reflecting member before and after the reflection between an S-polarizing component and a P-polarizing component with respect to the reflecting surface.

In the related art described above, in a polarization-sensitive OCT apparatus having a Mach-Zehnder interferometer, a reference light is reflected by a reference mirror at a right angle. Therefore, the phase of one polarization component is delayed from that of the other polarization component which may cause the phase difference between different polarization components.

Such a problem may occur not only in the mirror provided in a reference optical path, but also in a transmitting member such as an eyepiece provided on a measurement optical path, that is, not in fibers, but in an optical member arranged in air.

The polarization-sensitive OCT apparatus is capable of acquiring a polarization OCT image by detecting the phase difference between the different polarization components generated in an object to be examined. However, if there is a phase difference of polarization in the optical path of the optical OCT apparatus, it is difficult to achieve accurate detection of the phase difference between the different polarization components generated in the object to be examined.

This disclosure provides a reduction in a phase difference (phase delay) between different polarization components generated by reflection or transmission (specifically, reflection of a reflecting member) of an optical member provided on an optical path. Accordingly, the phase difference between the different polarization components generated by the optical member provided in an optical path may be corrected.

According to an embodiment, a reduction in a phase difference (phase delay) between the different polarization components generated by reflection or transmission (specifically, reflection of the reflecting member) of the optical member provided on the optical path is achieved.

A correcting device configured to correct the phase difference between the different polarization components is an optical member of the same type as the optical member described above, and can be arranged so as to correct the phase difference. The optical member and the correcting device include, for example, a dichroic mirror provided on the optical path of a measurement light or a reference mirror provided on the optical path of the reference light.

The correcting device configured to correct the phase difference between the different polarization components includes an optical member of a type different from the optical member described above, and can include a driving device configured to drive the correcting device, and a control device configured to control the driving device so as to correct the phase difference. The correcting device includes, for example, a λ/2 plate or a λ/4 plate as an example of a polarization adjusting member, and a driving device such as a motor rotates the polarization adjusting member.

The correcting device includes, for example, a polarizer (a third embodiment), a liquid-crystal optical element (a fourth embodiment), and a fiber-type polarization control member (a fifth embodiment).

In the case where the optical member is provided on the optical path of the measurement light, the correcting device can be provided on the optical path of the measurement light. Accordingly, the phase difference between the different polarization components generated in the measurement light can be corrected in the optical path of the measurement light. In the case where the optical member is provided on the optical path of the reference light, the correcting device can be provided on the optical path of the reference light. Accordingly, the phase difference between the different polarization components generated in the reference light can be corrected in the optical path of the reference light. Accordingly, the correction of the phase difference between the different polarization components can be simply configured.

Referring now to the drawings, an embodiment of this disclosure will be described in detail.

First Embodiment: Phase Difference in Polarization Generated in Optical Member is Corrected by an Optical Member of the Same Type Referring now to FIGS. 1, 2 and FIG. 4, the configuration of the polarization-sensitive OCT apparatus in this embodiment will be described. For the sake of convenience, X-, Y-, and Z-axes are set as illustrated in the drawings.

General Configuration of Apparatus

Figure 1:
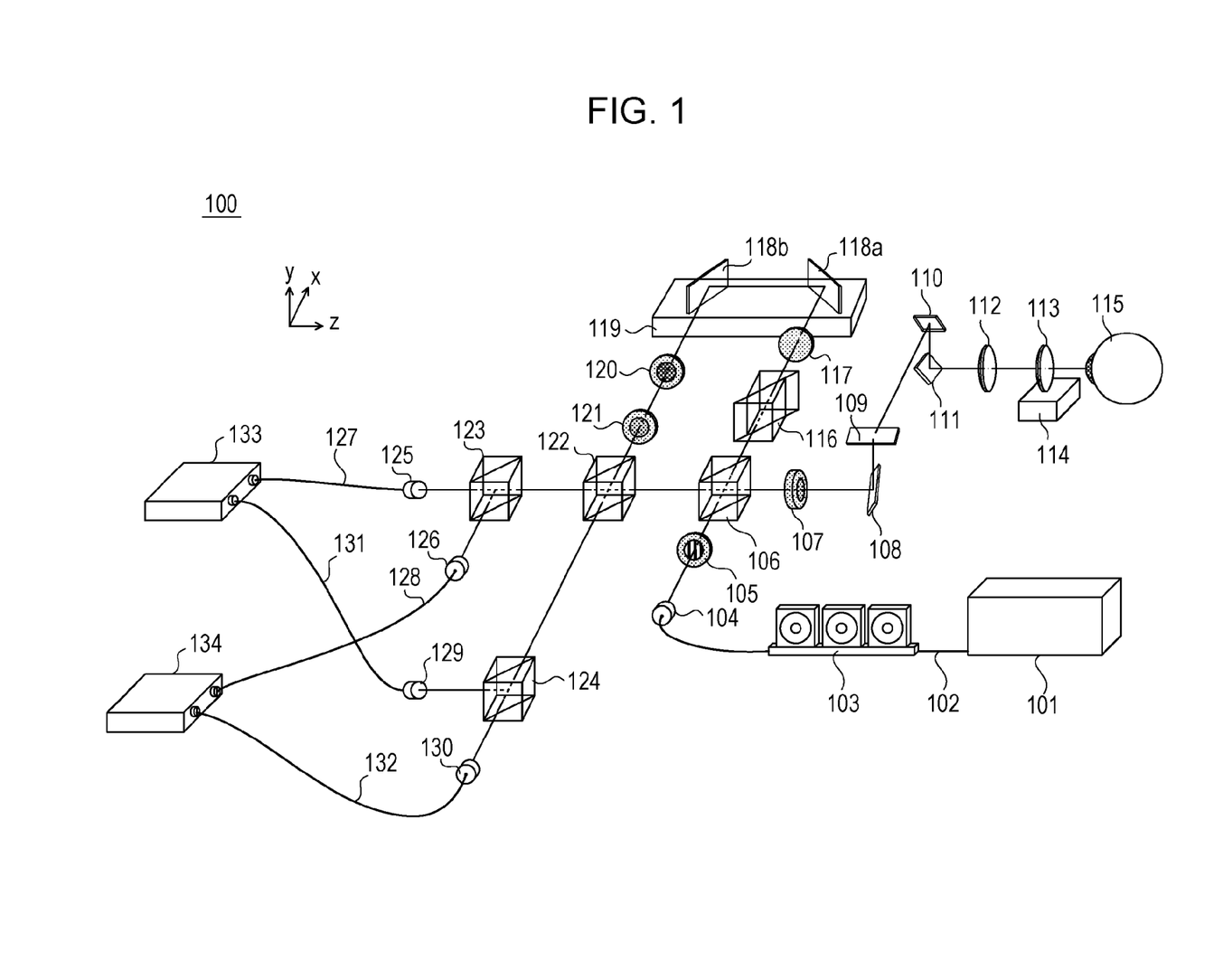
FIG. 1 is a schematic drawing illustrating a general configuration of an SS-PS-OCT apparatus configured as a bulk system according to a first embodiment.

FIG. 1 is a schematic drawing illustrating a general configuration of a polarization-sensitive OCT apparatus of this embodiment, and is an example of the configuration of an SS (Swept Source)-PS (Polarization sensitive)-OCT apparatus including a Mach-Zehnder interferometer.

Configuration of SS-PS-OCT Apparatus 100

A configuration of an SS-PS-OCT apparatus 100 will be described. A light source 101 includes a wavelength sweeping light source in which an oscillation wavelength of light changes periodically and, for example, emits light having a center wavelength of 1040 nm, and a band width of 100 nm. The light emitted from the light source 101 is guided to a collimator 104 via a single mode fiber (hereinafter referred to as "SM fiber") 102, and a polarization controller 103, and a collimated light is emitted to a space in the collimator 104. The emitted collimated light is guided to a beam splitter 106 via a polarizer 105, and is split into a measurement light (also referred to as an OCT measurement light) and a reference light (also referred to as a reference light corresponding to the OCT measurement light). The split ratio of the beam splitter 106 is 90 (reference light):10 (measurement light). The split ratio is not limited to these values, and other values are also applicable.

The polarization controller 103 is configured to correct the polarization of light emitted from the light source 101 so as to be a desired polarized state. The polarization controller 103 is, for example, a fiber-type polarization controller including a paddle type configured to correct the polarization by tilting respective paddles, which have fiber wounded in a coiled state, or an in-line type configured to correct the polarization by pressing and rotating the fibers. A bulk type polarization controller configured to emit light from a fiber to a space and correct the polarization by using a ½ wavelength plate and a ¼ wavelength plate is also applicable. In this embodiment, the light from the light source 101 is corrected into a linearly-polarized beam by the polarization controller 103. In the case where a degree of polarization of the light source 101 is not high, the degree of polarization of the light emitted from the light source 101 may be increased by arranging the polarizer 105 as illustrated in FIG. 1. In this case, by adjusting the polarization controller 103, an amount of light to be transmitted by the polarizer 105 may be adjusted. A configuration in which the polarization controller 103 is not arranged and the collimator 104 is connected to the SM fiber 102 is also applicable. In this case, the polarized state of the light emitted from the light source 101 does not need to be corrected, and hence only the degree of polarization can be increased. However, depending on the polarized state of the light, an amount of light guided by the interferometer may be reduced. Therefore, whether the amount of light is sufficient or not needs to be confirmed. Examples of a method of confirming the amount of light include a method of measuring a collimated light after having passed through the polarizer 105 with a power monitor, and determining whether or not the amount of light is not smaller than a certain amount of light, or a method of determining whether a sufficient and required amount of light is detected by detectors 133 or 134.

Measurement Optical Path

A split measurement light passes through a ¼ wavelength plate 107, and is reflected by a Y-direction scanning Galvano scanner 108 configured to scan in a Y-direction the measurement light at a position of a pupil and an X-direction scanning Galvano scanner 109. The measurement light changed in pathway by the Galvano scanners 108 and 109 is further reflected by dichroic mirrors 110 and 111, and enters an eye to be examined 115 via a scan lens 112 and an objective lens 113. In this embodiment, the ¼ wavelength plate 107 is arranged so as to achieve a circularly polarized beam at the eye to be examined 115. The objective lens 113 is fixed onto a stage 114, and moves in a direction of an optical axis, so that adjustment of diopter scale of the eye to be examined is achieved. Although not illustrated, the Galvano scanners 108 and 109 and the stage 114 are controlled by a drive control unit, and are capable of scanning the measurement light within a desired range of the eye to be examined 115 (also referred to as the range of acquirement of a tomographic image, a position of acquirement of a tomographic image, and an irradiating position of the measurement light). The measurement light enters the eye to be examined 115 by the objective lens 113 placed on the stage 114 and is focused on an eyeground. The measurement light with which the eyeground is irradiated is reflected and scattered by respective retina layers, follows the above-described optical route, and enters a beam splitter 122 via the beam splitter 106. The reflected measurement light is reflected by an X-Y plane in the Galvano scanner 109, then is reflected by a Y-Z plane in the Galvano scanner 108.

In the polarization-sensitive OCT apparatus, in the same manner as the general OCT apparatus, there is a conceivable case where a multiple wavelength light, such as an SLO (Scanning Laser Ophthalmoscopy) beam for acquiring a fixation lamp or an eyeground image, and an observation light for observing an anterior eye part, other than the OCT measurement light, enters the eye to be examined 115. In such a case, a dichroic mirror configured to selectively reflect and transmit the wavelength in the measurement optical path is arranged. Therefore, the measurement light is also reflected by the dichroic mirrors 110 and 111 as well, and hence changes the pathway.

Reference Optical Path

In contrast, the reference light split by the beam splitter 106 is reflected by mirrors 118a and 118b on a coherence gate stage 119 via a dispersion compensation glass 116 and an ND filter 117. The reference light is attenuated via the ND filter 117, and is adjusted to a range so that an interfering light does not exceed a measurement range of the detector. The coherence gate stage 119 corresponds to a difference of an axial length of the eyeball of the subject, and hence is controlled by the drive control unit (not shown), and is moved in an X-direction in FIG. 1 to be adjusted. The mirrors 118a and 118b are arranged so as to reflect the reference light in the X-Z plane. In contrast, since the reference light is a linearly-polarized beam vibrating in the Y-direction, the reference light does not have an S-polarizing component with respect to the reflecting surfaces of the mirrors 118a and 118b. In other words, the reflection does not cause any phase difference between the S-polarization and P-polarization and the polarized state may be maintained constant. Therefore, the phase delay may be suppressed by causing the reference light having only the S-polarizing component or only the P-polarizing component to enter the reflecting surfaces of the mirrors 118a and 118b.

The reference light reflected by the mirrors 118a and 118b enters the beam splitter 122 via a ¼ wavelength plate 120 and a ½ wavelength plate 121. A direction of vibrations of light passing through the ½ wavelength plate can be changed as desired by rotating the ½ wavelength plate by a predetermined angle before arrangement. In this embodiment, the ½ wavelength plate 121 is arranged so that the polarized states of the reference lights entering polarization beam splitters 123 and 124 become linearly-polarized beams inclined by 45° with respect to two polarization axes that are orthogonal to each other.

Detection Optical Path

The measurement light and the reference light that have entered the beam splitter 122 are combined and become an interfering light, which is split at a split ratio of 50:50. The beam splitter 122 is an example of a splitting device that splits light into a plurality of lights having different polarization components. The split interfering light has amplitude phases inverted from each other (hereinafter, referred to as "positive component" and "negative component"), and the positive interfering light is guided to the polarization beam splitter 123, and the negative interfering light is guided to the polarization beam splitter 124. In the polarization beam splitters 123 and 124, the interfering light is split so as to match the two polarization axes that are orthogonal to each other, and is split into two lights having a horizontal polarization component (hereinafter, referred to as an H component) and a vertical polarization component (hereinafter, referred to as a V component). The H-components of both of the positive and negative interfering lights split by the polarization beam splitters 123 and 124 are received by light-receiving collimators 125 and 129 enter the detector 133 via SM fibers 127 and 131, and the detector 133 detects the differential thereof. The detectors 133 and 134 are examples of the detecting device configured to detect a plurality of lights having different polarization components. In contrast, the V-components of the interfering light are received by light-receiving collimators 126 and 130, and enter the detector 134 via SM fibers 128 and 132. The lights received by the detectors 133 and 134 are output as electric signals in accordance with light intensities.

In this embodiment, by making the reference light a linearly-polarized beam at an angle of 45° with respect to two polarization axes that are orthogonal to each other, the reference light is split into lights having the H-components and the V-components equivalent to each other. In this embodiment, since the measurement light is a circularly polarized beam, simultaneous acquirement is achieved irrespective of directions of cells and fibers of the eyeground of the eye to be examined 115. Consequently, acquirement of data on all of directions of polarization is enabled at once, so that the necessity of imaging the same position from each of the directions of polarization is eliminated and the data can be acquired at one go.

In this embodiment, mirrors are installed for reflecting lights, but any member may be employed as long as lights can be reflected. For example, the same effects and advantages are achieved with a right angle prism.

Although the example of the configuration of the bulk-system of the SS-PS-OCT has been described, this disclosure is not limited thereto, and a fiber-system can be also employed. In such a case, as illustrated in FIG. 2, the same effects and advantages are achieved by arranging the polarizer 105, beam splitters 106 and 122, and the polarization beam splitters 123 and 124 in the in-line type arrangement.

Configuration of SS-PS-OCT Apparatus 200

Figure 2:
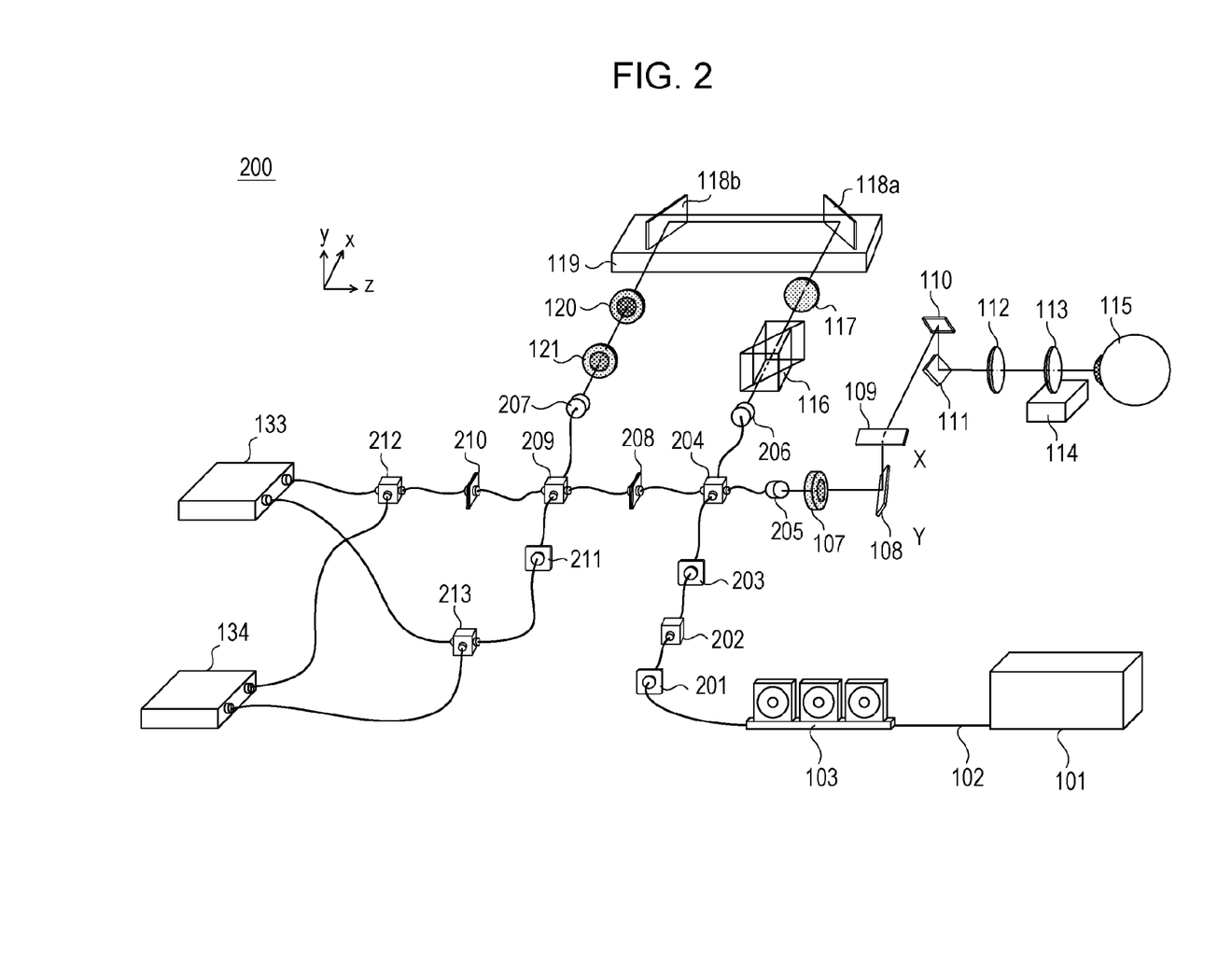
FIG. 2 is a schematic drawing illustrating a general configuration of the SS-PS-OCT apparatus configured as a fiber system according to the first embodiment.

With reference to FIG. 2, a configuration of an SS-PS-OCT apparatus 200 will be described. Detailed description of portions having the same configurations as those of the SS-PS-OCT apparatus 100 (FIG. 1) will be omitted.

The SM fiber 102 is connected to a polarizer 202 via a connector 201. Fibers from the polarizer 202 onward are Polarization Maintaining: PM fiber (hereinafter, referred to as "PM fiber"), so that the polarized state can be maintained. The polarizer 202 is connected to a beam splitter 204 via a connector 203, and the beam splitter 204 is connected to a measurement light emitting collimator 205, a reference light emitting collimator 206, and a connector 208. A split ratio of the beam splitter 204 is 90(reference light):10 (measurement light). The split ratio is not limited to these values, and other values are also applicable.

Measurement Optical Path

The split measurement light is emitted from the collimator 205, and enters the eye to be examined 115 via the ¼ wavelength plate 107, the Galvano scanners 108 and 109, the dichroic mirrors 110 and 111, the scan lens 112, and the objective lens 113. The measurement light with which the eye to be examined 115 is irradiated is reflected and scattered by respective retina layers, follows the optical route, which is the same as the optical route at the time of incidence, and enters a beam splitter 209 via the beam splitter 204.

Reference Optical Path

In contrast, the reference light is emitted from the collimator 206, is reflected by the mirrors 118a and 118b on the coherence gate stage 119 via the dispersion compensation glass 116 and the ND filter 117, is received by a collimator 207 via the ¼ wavelength plate 120 and the ½ wavelength plate 121, and enters the beam splitter 209.

Detection Optical Path

A split ratio of the beam splitter 209 is 50:50. The incident end is connected to a reference light receiving collimator 207 and the connector 208, and an output end is connected to polarization beam splitters 212 and 213 via connectors 210 and 211. An H component of the interfering light split by the polarization beam splitters 212 and 213 enters an input terminal of the detector 133, and on the other hand, the V-components of the interfering light enters an input terminal of the detector 134.

In this configuration, the SS-PS-OCT apparatus 100 of the bulk system may be changed into the SS-PS-OCT apparatus 200 of the fiber system.

An Example of Correcting Device of Phase Difference in Polarization: Correction by Galvano Scanner of the Same Type At this time, the phase of the S-polarizing component is delayed with respect to the reflecting surface of the Galvano scanner 108, which is an example of a first scanning device, and in the same manner, the phase of the S-polarizing component is delayed with respect to the reflecting surface of the Galvano scanner 109 as an example of a second scanning device. Here, an incident surface of the Galvano scanner 108 for the measurement light and an incident surface of the Galvano scanner 109 are orthogonal to each other. Therefore, the polarization component which may be delayed in phase by a reflection from the Galvano scanner 108 and the polarization component which may be delayed in phase by a reflection from the Galvano scanner 109 are reversed, and as a consequence, the phase difference in polarization generated by the reflection is canceled out.

Figure 4:
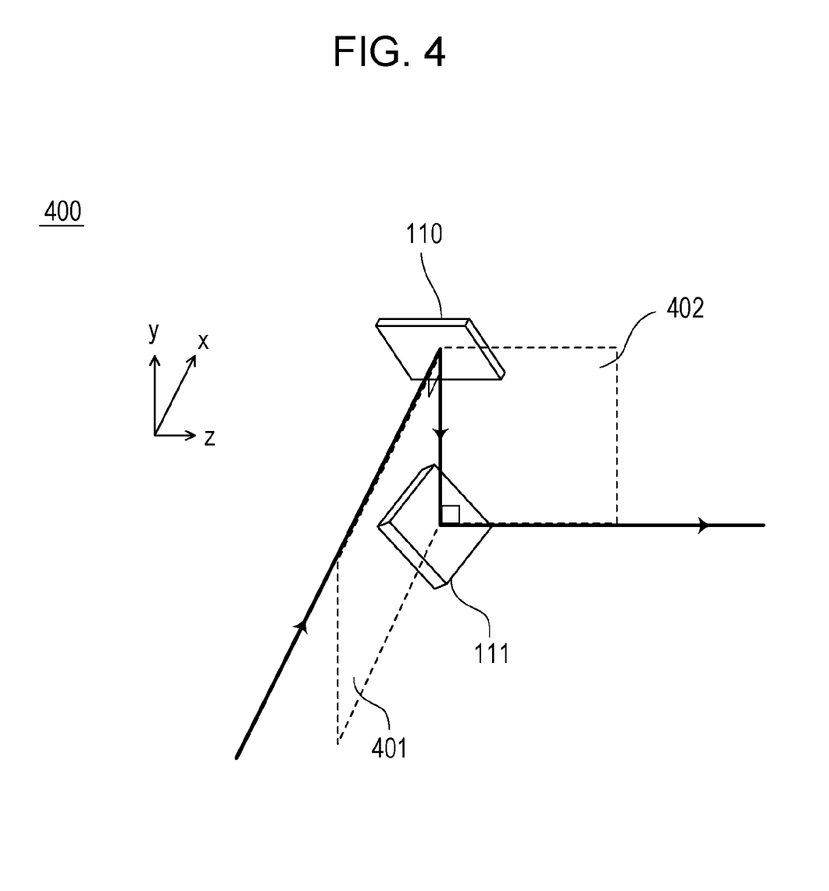
FIG. 4 is a schematic drawing explaining an arrangement of a dichroic mirror for correcting phase delay of polarization in a measurement optical path of the SS-PS-OCT apparatus of the first embodiment.

An Example of Correcting Device of Phase Difference in Polarization: Correction by Dichroic Mirror of the Same Type An amount of delay in phase of the polarization generated by the reflection and transmission of the dichroic mirror, which is an example of a wavelength selecting unit, varies depending on the wavelength. Therefore, it is difficult to perform correction by using signal processing. Therefore, a method of installing the same dichroic mirror separately in a measurement optical path, and causing the light to be reflected so as to cancel out the phase delay of the polarization is desirable. Specifically, as illustrated in FIG. 4, the dichroic mirrors 110 and 111 are arranged so as to reflect the measurement light in an X-Y plane 401 in the dichroic mirror 110, which is an example of a first wavelength selecting member, and then reflect the measurement light in a Y-Z plane 402 in the dichroic mirror 111, which is an example of a second wavelength selecting member. When an incident surface 401 with respect to the dichroic mirror 110 and an incident surface 402 with respect to the dichroic mirror 111 are orthogonal to each other in the same manner as the Galvano scanners 108 and 109, the S-polarizing component which is subjected to the phase delay due to the reflection by the dichroic mirror 110 and the S-polarizing component which is subjected to the phase delay due to the reflection by the dichroic mirror 111 are also orthogonal to each other. Therefore, with the reflection of two times, the phase difference generated by each of the reflection can be canceled out. In both of the examples above where the correction is made by the Galvano scanners 108 and 109 or the dichroic mirrors 110 and 111, the first reflecting member and the second reflecting member are provided so that a first incident surface defined by an incident light on a boundary surface of the first reflecting member and a reflecting light therefrom, and a second incident surface defined by an incident light on a boundary surface of the second reflecting member and a reflecting light therefrom intersect each other. In other words, the first reflecting member and the second reflecting member are arranged so that the incident surfaces defined by the incident lights on the boundary surfaces and the reflecting lights therefrom, which are the incident surface of the first reflecting member and the incident surface of the second reflecting member intersect each other. In other words, the second reflecting member includes the second incident surface which intersects the first incident surface defined by the incident light on the boundary surface of the first reflecting member and the reflecting light therefrom, and is arranged so as to correct the phase difference between the different polarization components generated by the first reflecting member.

An Example of Correcting Device for Correcting Phase Difference in Polarization: Correction by Wavelength Plate as an Example of Polarization Adjusting Member Here, it is considered where the polarized state of the reference light is polarized including the S-polarizing component and the P-polarizing component with respect to the reflecting surface instead of the linearly-polarized beam including only one of the S-polarizing component or the P-polarizing component. In this case, a phase difference in polarization may be generated by the reflection of the mirror 118a and the mirror 118b, so that an elliptically polarized beam may result.

In this case, since the elliptically polarized beam is caused by the reflection, the ¼ wavelength plate 120 may be arranged between the mirror 118b and the ½ wavelength plate 121 and correction may be made to achieve a linearly-polarized beam. In this embodiment, an example in which the ¼ wavelength plate 120 is used for correcting the polarization will be described. However, the correction from the elliptically polarized beam to the linearly-polarized beam does not have to be done by the ¼ wavelength plate 120. For example, any members such as a polarizer, a liquid-crystal optical element, an electronic optical element, and a fiber-type polarization controller may be employed as long as the reference light can be corrected to the linearly-polarized beam.

A configuration in which the phase difference in polarization generated by the mirror 118a or 118b provided on the optical path of the reference light is corrected by using one of the polarization adjusting members without providing a plurality of polarization adjusting members including the ¼ wavelength plate 120 and the ½ wavelength plate 121 on the optical path is also applicable. A configuration in which the polarized state is adjusted by controlling the ½ wavelength plate 121 so as to be rotated by the driving device such as the motor, is also applicable. Specifically, the configuration in which the polarized state, by using the ½ wavelength plate 121, is adjusted by rotating the ½ wavelength plate, by the driving device such as a motor, so that the signal intensities detected by the detectors 133 and 134 become substantially the same. In this case, for example, the light is blocked between the objective lens 113 and the eye to be examined 115 to prevent the measurement light from returning to the detectors 133 and 134, so that detection of only the signal intensity of the reference light is achieved. However, since the interference signal is required in the case of performing detection by differential detection, for example, a Fabry-Perot interference system is built by arranging a thin glass plate having a thickness on the order of 1 mm to several mm in the reference optical path, and an interference signal of the reference light is generated by multiple reflection to achieve differential detection. Whether or not the reference light is rightly corrected may be confirmed, for example, by arranging a polarization measuring instrument before the beam splitter 122, and monitoring the polarized state of the reference light.

According to the configuration described above, even in the case where the phase difference (phase delay) in polarization is generated due to the influence of reflection and transmission of the optical member, the polarized state can be corrected. Therefore, polarization characteristics of the eye to be examined can be measured with high degree of accuracy.

Second Embodiment: Phase Difference in Polarization Generated in Optical Member is Corrected by an Optical Member of the Same Type A second embodiment will be described with reference to FIG. 3. In the first embodiment, the example of the configuration of the SS-PS-OCT has been described. However, this disclosure is not limited thereto, and a spectrum domain OCT (hereinafter, referred to as SD-OCT) is also applicable. With the configuration of the SD-PS-OCT according to this embodiment, the phase difference (phase delay) in polarization generated in the optical member can be corrected. In the first embodiment, the example of the configuration using the interferometer of the Mach-Zehnder type has been described. However, a configuration using a Michelson interferometer as this embodiment is also applicable.

Configuration of SD-PS-OCT Apparatus 300

Figure 3:
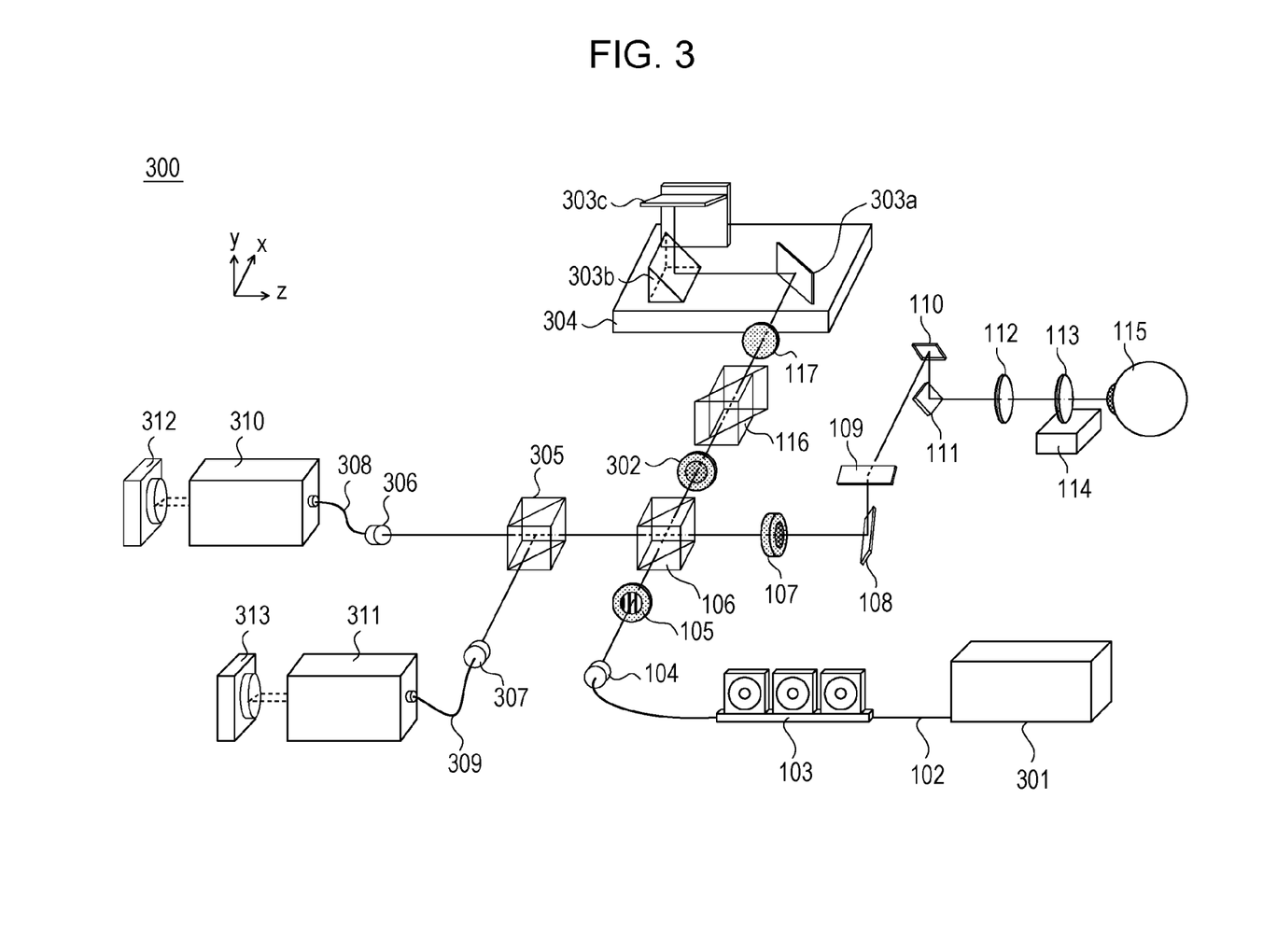
FIG. 3 is a schematic drawing illustrating a general configuration of an SD-PS-OCT apparatus according to a second embodiment.

With reference to FIG. 3, a configuration of an SD-PS-OCT apparatus 300 will be described. Detailed description of portions having the same configurations as those of the SS-PS-OCT apparatus 100 of the first embodiment will be omitted.

A light source 301 is an SLD (Super Luminescent Diode) light source, which is a low coherent light source, and emits light having a center wavelength of 850 nm and a band width of 50 nm, for example. Although the SLD is used as the light source 101, any light source may be used as long as the light source can emit a low coherent light such as an ASE (Amplified Spontaneous Emission) light source. The light emitted from the light source 301 is guided to the collimator 104 via the SM fiber 102, and the polarization controller 103, and a collimator light is emitted to a space in the collimator 104. The emitted collimated light is guided to a beam splitter 106 via a polarizer 105, and is split into a measurement light and a reference light. A split ratio of the beam splitter 106 is 90(reference light):10 (measurement light). The split ratio is not limited to these values, and other values are also applicable.

Measurement Optical Path

The split measurement light enters an eye to be examined 115 via the ¼ wavelength plate 107, the Galvano scanners 108 and 109, the dichroic mirrors 110 and 111, the scan lens 112, and the objective lens 113. The measurement light with which the eye to be examined 115 is irradiated is reflected and scattered by respective retina layers, follows the above-described optical route, and enters a beam splitter 305 via the beam splitter 106.

Reference Optical Path

In contrast, the split reference light is reflected by mirrors 303a, 303b, and 303c provided on a coherence gate stage 304 via a ¼ wavelength plate 302, a dispersion compensation glass 116 and an ND filter 117. The coherence gate stage 304 moves in the X-direction in FIG. 3, and hence can adjust a gate position. The arrangement of the mirrors is not limited thereto. For example, a configuration in which the mirror 303a is demounted from the coherence gate stage 304 and is fixed is also applicable. In this case, a position of a coherence gate can be adjusted by moving the coherence gate stage 304 in the Z-direction in FIG. 3. In the same manner, a configuration in which the mirrors 303a and 303b are demounted from the coherence gate stage 304 and are fixed is also applicable. In this case, the position of the coherence gate can be adjusted by moving the coherence gate stage 304 in the Y-direction in FIG. 3. The ¼ wavelength plate 302 is arranged so that the polarized state of the reference light entering a polarization beam splitter 305 becomes a linearly polarized beam inclined by 45° with respect to two polarization axes on a divided surface. By installing the ¼ wavelength plate 302 so as to be inclined by 22.5° from the P-polarization with respect to the S-polarization about an optical axis of the reference light as an axis of rotation, the polarized state when the reference light is returned and enters the polarization beam splitter 305 may be corrected to a linearly polarized beam inclined by 45° with respect to the two polarization axes.

Detection Optical Path

The measurement light and the reference light that have entered the beam splitter 106 are combined and become an interfering light, and enter the polarization beam splitter 305. In the polarization beam splitter 305, the interfering light is split along the two polarization axes that are orthogonal to each other, and is split into two lights having the H component and the V component. The H-components of the interfering light are received by a light-receiving collimator 306, and is detected by a detector 312 via a SM fiber 308 and a spectroscope 310. In contrast, the V-components of the interfering light are received by a light-receiving collimator 307, and is detected by a detector 313 via an SM fiber 309 and a spectroscope 311. In this embodiment, an example of the configuration including the SM fibers 308 and 309 is illustrated. However, a configuration including a PM fiber instead of the SM fibers 308 and 309 is also applicable.

An Example of Correcting Device of Phase Difference in Polarization: Correction by Mirror of the Same Type In the case where the PS-OCT apparatus is a Michelson interferometer, the reference light is reflected by the reference mirror, follows the same optical path, and returns back to the beam splitter 106. Therefore, the reference light needs to be corrected to a desired polarized state at the position of the beam splitter 106 that interferes with the measurement light by being corrected in polarized state by the ¼ wavelength plate 302 in both directions (forward and reflected), that is, twice in total.

At this time, in the case where the reference optical path is configured only by a reflection within a X-Z plane, the reference optical path is influenced by the phase delay of the polarization by the reflection, so that it is difficult to correct the polarized state of the reference light after having gone and back to a desired polarized state. Therefore, as illustrated in FIG. 3, the reference light is reflected by the mirror 303a, which is an example of a first reflecting member, in an X-Z plane at a right angle. The X-Z plane is a plane including the optical axis of the optical path where the mirror 303a is provided. The reference light is also reflected by the mirror 303b, which is an example of a second reflecting member, in the Y-direction, which is a direction of a normal line as an example of the direction intersecting the X-Z plane. Accordingly, the second reflecting member may be provided so as to correct the phase difference between the different polarizing components generated by the first reflecting member, such that the phase delay in polarization can be canceled out. The first reflecting member and the second reflecting member are provided so that a first incident surface defined by an incident light on a boundary surface of the first reflecting member and a reflecting light therefrom, and a second incident surface defined by an incident light on a boundary surface of the second reflecting member and a reflecting light therefrom, intersect each other. In other words, the first reflecting member and the second reflecting member are arranged so that the incident surfaces defined by the incident lights on the boundary surfaces and the reflecting lights therefrom, which are the incident surface of the first reflecting member and the incident surface of the second reflecting member intersect each other. In other words, the second reflecting member includes the second incident surface which intersects the first incident surface defined by the incident light on the boundary surface of the first reflecting member and the reflecting light therefrom, and is arranged so as to correct the phase difference between the different polarization components generated by the first reflecting member. The mirror 303c is fixed onto the coherence gate stage 304 with, for example, a fixing jig, and is arranged so as to reflect and return the reference light guided from the mirror 303b in the same direction.

Canceling out of the phase difference completely is limited to the case where the mirror 303a and 303b have the same refractive index. When canceling out by the reflecting surfaces having different refractive indexes, the reflecting angles of the mirrors 303a, 303b, and 303c need to be adjusted so that the polarized state at the reflecting point of the mirror 303c becomes a desired state.

An Example of Correcting Device of Phase Difference in Polarization: Correction by Rotation of ¼ Wavelength Plate At this time, a configuration in which the polarized state is adjusted by controlling the ¼ wavelength plate 302 so as to be rotated by the driving device such as the motor is also applicable. In this case, for example, the mirrors 303a, 303b, and 303c may be configured so as to return the reference light to the beam splitter 106 by one regular reflection by using one mirror. As a matter of course, both of the configurations in which the ¼ wavelength plate 302 is rotated and the mirrors 303a, 303b, and 303c are provided as in this embodiment, may be employed.

Specifically, the configuration in which the polarized state by using the ¼ wavelength plate 302 is achieved by rotating the ¼ wavelength plate so that the signal intensities detected by detectors 312 and 313 become substantially the same. In this case, for example, the light is blocked between the objective lens 113 and the eye to be examined 115 to prevent the measurement light from returning to the detectors 133 and 134, so that detection of only the signal intensity of the reference light is achieved. The SD-PS-OCT apparatus 300 employs a system of detecting the split light by a CCD line sensor. As described in conjunction with the SS-PS-OCT apparatus 100, since the interference signal is required in the case of a differential detection system, it is necessary to build a Fabry-Perot interference system by arranging a thin glass plate in the reference optical path and generate an interference signal of the reference light by multiple reflection to achieve differential detection. However, the detecting method using the CCD line sensor is capable of acquiring a light signal intensity even though it is not an interference signal, and hence a glass plate does not need to be arranged in the reference optical path.

With the configuration of the correcting device configured to correct the phase difference in polarization as described above, the phase difference (phase delay) of the polarization generated by the optical member may be corrected also in the SD-PS-OCT apparatus. The correcting device in the PS-OCT apparatus of this embodiment may be applied as the correcting device in the PS-OCT apparatus of the first embodiment.

Third Embodiment: Polarizer is Applied as Correcting Device for Correcting the Phase Difference of Polarization A third embodiment will be described with reference to FIG. 5. In the first embodiment, the ¼ wavelength plate 120 is applied as the correcting device configured to correct the phase difference in polarization in the reference light path of the PS-OCT apparatus. However, the correcting device is not limited thereto. This embodiment is an example in which a polarizer 501 is applied as the correction device. The configuration of the first to the third embodiments may be applied to portions other than the reference optical path.

Figure 5:
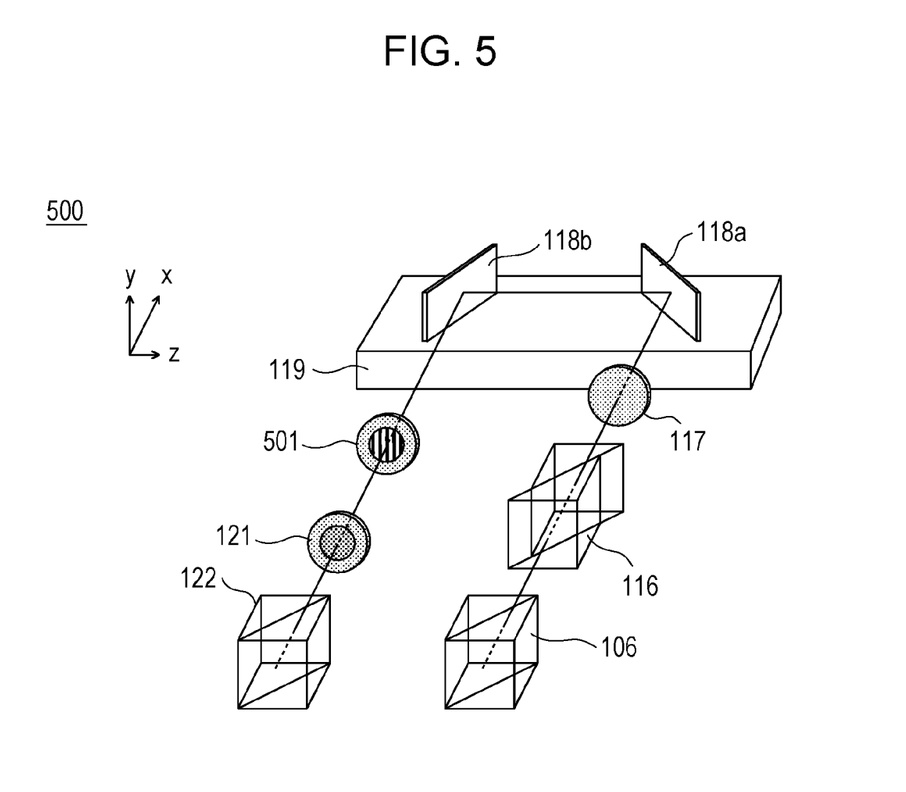
FIG. 5 is a schematic drawing illustrating a case where a polarizer is applied as a correcting device for correcting the phase difference of polarization in a reference optical path of the PS-OCT apparatus of a third embodiment.

Since the polarizer 501 transmits only the linearly polarized beam vibrating in a specific direction from the reference light which has become an elliptically polarized beam, an amount of light of the reference light is attenuated. The attenuation of the amount of the reference light is compensated by the adjustment of an amount of attenuation by an ND filter 117. In other words, the amount of attenuation by the ND filter 117 may be adjusted by an amount of light attenuated by the polarizer 501. In other words, also in the case where the amount of reference light is attenuated by the transmission through the polarizer 501, the polarizer 501 may be arranged so that a sufficient interference intensity with respect to measurement ranges of the detector 133 or 134, and a fine adjustment of the amount of light may be performed by the ND filter 117. For example, the polarizer 501 is arranged while adjusting a direction of slits so as to align with a long axis of the elliptical polarization of the reference light. By arranging the polarizer 501 so that the direction axis of the elliptically polarized beam and the slits of the polarizer 501 are aligned, the reference light can be corrected to the linearly polarized beam at the highest transmittance. A method of adjustment includes arranging the polarizer 501, and rotating the direction of the slits of the polarizer 501 so that an interference signal detected by the detectors 133 and 134 becomes the strongest. The reference light which has passed through the polarizer 501 and has the linearly polarized beam is corrected in the direction of vibration by the ½ wavelength plate 121 provided downstream of the polarizer 501. An adjustment of the ½ wavelength plate 121 in the same manner as in the first embodiment is performed so that the polarized state of reference lights entering polarization beam splitters 123 and 124 becomes linearly polarized beams inclined by 45° with respect to two polarization axes. Here, in order to rotate the direction of the slits of the polarizer 501, a configuration in which the slits are driven by the driving device such as the motor, a control device, which is not illustrated, controls the driving device so as to rotate the direction of the slits is applicable.

The ½ wavelength plate 121 does not have to be used in the case where a correction to make the interference signal have a sufficient interference intensity, and the polarized state of the reference light to become the linearly polarized beam inclined by 45° with respect to the two polarization axes that are orthogonal to each other by using only the polarizer 501, is possible.

In the case where the polarizer 501 is applied as the correcting device in the reference optical path of the PS-OCT apparatus as described above, the phase difference (phase delay) of the polarization generated by the optical member may be corrected also in case where the polarizer 501 is applied as the correcting device in the reference optical path of the PS-OCT apparatus.

Fourth Embodiment: Liquid-Crystal Optical Element is Applied as Correcting Device for Correcting the Phase Difference of Polarization A fourth embodiment will be described with reference to FIG. 6. This embodiment is an example in which a liquid-crystal optical element 601 is applied as a correcting device for correcting the phase difference of polarization in the reference optical path of the PS-OCT apparatus. The configuration of the first to the third embodiments may be applied to portions other than the reference optical path.

Figure 6:
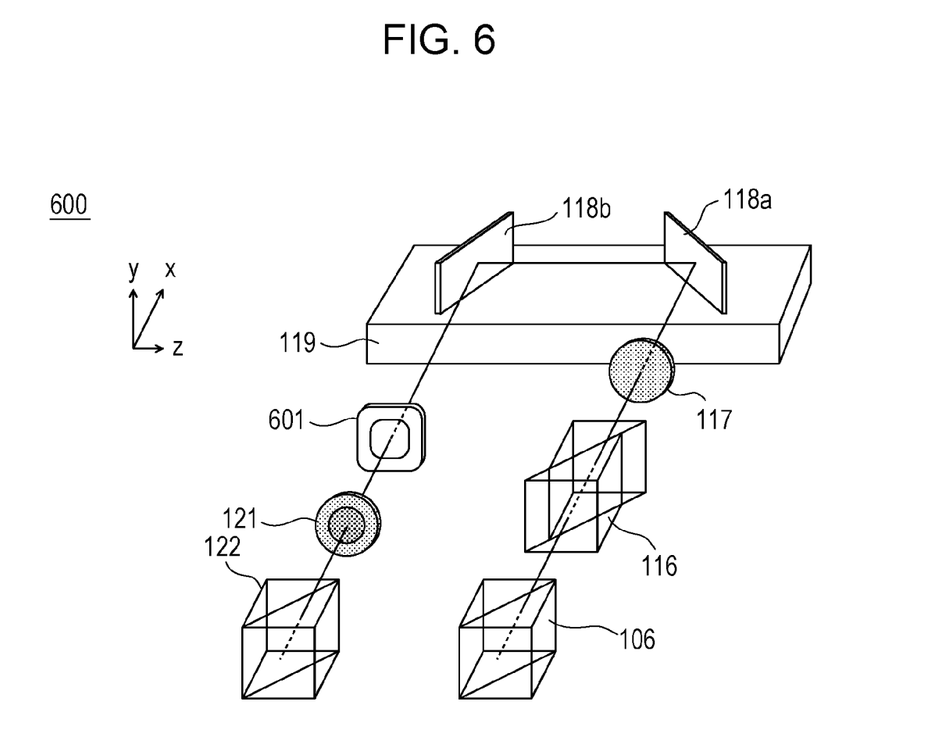
FIG. 6 is a schematic drawing illustrating a case where a liquid-crystal optical element is applied as the correcting device for correcting the phase difference of polarization in the reference optical path of the PS-OCT apparatus of a fourth embodiment.

For example, a transmissive liquid-crystal variable wavelength plate is used as the liquid-crystal optical element 601 and is arranged between the mirror 118b and the ½ wavelength plate 121. The liquid-crystal variable wavelength plate has cells filled with liquid crystal molecular solution, and the phase of the reflecting light or the transmitting light can be modulated by applying a predetermined voltage to the cells. In this embodiment, the phase delay generated by the reflection of the mirrors 118a and 118b is corrected and the voltage to be applied to the cells is adjusted so that the reference light becomes a linearly polarized beam. Here, the driving device, which is not illustrated can be controlled so that the control device, which is not illustrated, adjusts the voltage that the driving device applies to the liquid-crystal optical element 601.

The reference light which has become the linearly polarized beam by the liquid-crystal optical element 601 is corrected in a direction of vibration by the ½ wavelength plate 121 provided downstream of the liquid-crystal optical element 601. An arrangement of the ½ wavelength plate 121 in the same manner as in the first embodiment is performed so that the polarized state of reference lights entering polarization beam splitters 123 and 124 are output as linear polarizations inclined by 45° with respect to two polarization axes that are orthogonal to each other. In the same manner as the first embodiment, a configuration in which the polarized state is corrected by rotating the ½ wavelength plate 121 by the driving device such as a motor is also applicable.

In the case where the liquid-crystal optical element 601 is applied as the correcting device configured to correct the phase difference of the polarization in the reference optical path of the PS-OCT apparatus as described above, the phase difference (phase delay) in polarization generated by the optical member may be corrected also.

Fifth Embodiment: Fiber Type Polarization Controller is Applied as Correcting Device for Correcting the Phase Difference of Polarization A fifth embodiment will be described with reference to FIG. 7. This embodiment is an example in which a fiber type polarization controller 701 is applied as a correcting device for correcting the phase difference in polarization in the reference optical path of the PS-OCT apparatus. The configuration of the first to the third embodiments may be applied to portions other than the reference optical path.

Figure 7:
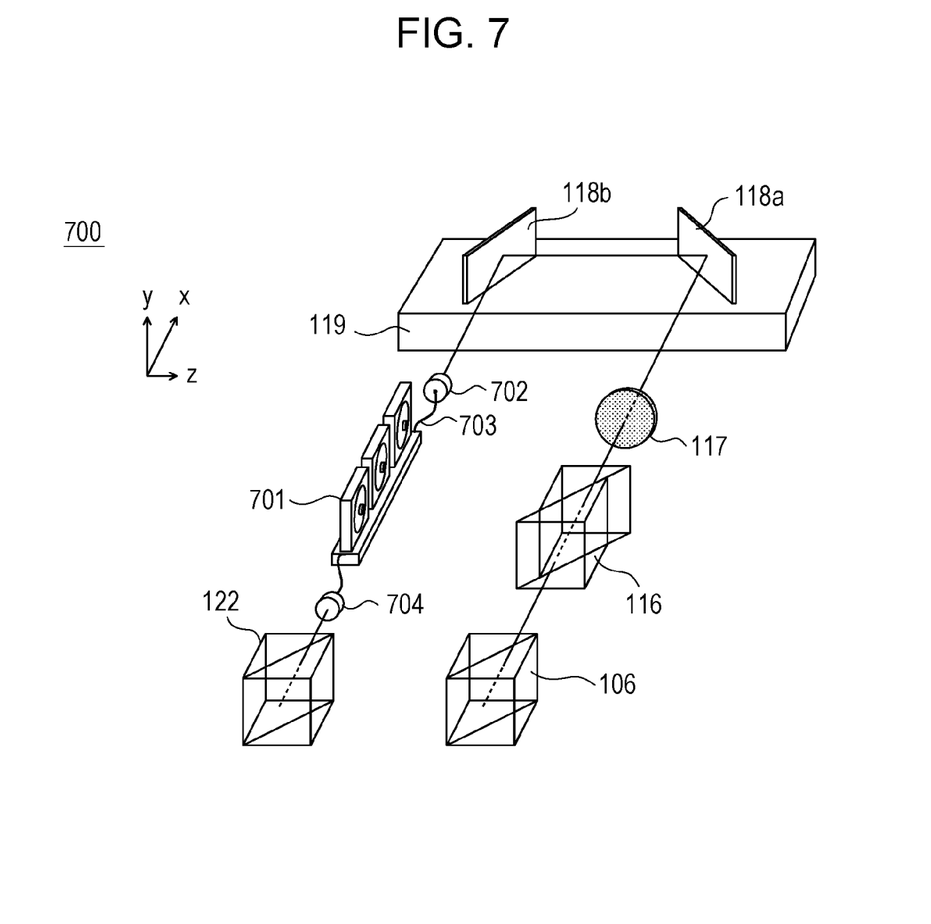
FIG. 7 is a schematic drawing illustrating a case where a fiber-type polarization controller is applied as a correcting device for correcting the phase difference of polarization in the reference optical path of the PS-OCT apparatus of a fifth embodiment.

In the case where the fiber type polarization controller 701 is used, the ½ wavelength plate 121 is demounted from the optical path because it is not necessary, and the polarization controller 701 is arranged between the mirror 118b and the beam splitter 122, so that a correction to a desired polarized state is achieved. In this case, the reference light needs to be received by a collimator 702. The reference light received by the collimator 702 is corrected in polarization by the polarization controller 701 via an SM fiber 703, and the polarized states of the reference lights entering the polarization beam splitters 123 and 124 are corrected so as to become a linearly polarized light inclined from each other by 45° with respect to the two polarization axes that are orthogonal to each other. The correction of the polarized state of the reference light by the polarization controller 701 is performed in the state in which the measurement light is blocked in the same manner as in the first embodiment, and is performed by adjusting the polarization to the signal intensities detected by the detectors 133 and 134 to be substantially the same. The reference light corrected in polarization by the polarization controller 701 is emitted from the collimator 704, and enters the beam splitter 122. Here, in the case where the polarization controller 701 controls the polarization by pressurizing (for example, oppression or rotation) the optical fiber with a knob or the like to control the polarization, a configuration in which the knob is driven by the driving device such as the motor, and the control device, which is not illustrated, controls the driving device is applicable.

As described thus far, in the reference optical path of the PS-OCT apparatus, the phase difference (phase delay) in polarization generated by the optical member may be corrected in the case where the fiber polarization controller 701 is applied as the correcting device configured to correct the phase difference of the polarization as well.

Other Embodiments

This disclosure can also be realized by executing the following processes. The process includes supplying software (program) which realizes functions of the above-described embodiments to a system or an apparatus via a network or various storage media, and reading out and executing the program by a computer (or a CPU or a MPU) of the system or the apparatus.

According to the present invention, the polarization-sensitive OCT apparatus of the above-described embodiments can image objects to be examined such as the skin or the teeth in addition to the anterior eye part or the eyeground of the eye to be examined. According to the present invention, the polarization-sensitive OCT apparatus of the above-described embodiments may be applied to a polarization SLO apparatus and a polarization eyeground camera.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to embodiments, it is to be understood that the invention is not limited to the disclosed embodiments. The scope of the following claims is to be accorded the broadest interpretation so as to encompass all such modifications and equivalent structures and functions.

This application claims the benefit of Japanese Patent Application No. 2014-125733 filed Jun. 18, 2014, which is hereby incorporated by reference herein in its entirety.

What is claimed is:

1. An imaging apparatus configured to image an object to be examined, comprising;
    a light splitting unit configured to split light obtained by combining a returned light from the object to be examined irradiated with a measurement light and a reference light corresponding to the measurement light into a plurality of lights having different polarization components;
    a detecting unit configured to detect the plurality of lights;
    a first reflecting member provided on an optical path the reference light;
    a second reflecting member provided on the optical path of the reference light so as to correct a phase difference between different polarization components generated by the first reflecting member;
    a third reflecting member provided on an optical path of the measurement light; and
    a fourth reflecting member provided on the optical path of the measurement light so as to correct a phase difference between different polarization components generated by the third reflecting member,
    wherein the first reflecting member and the second reflecting member are provided so that a first incident surface and a second incident surface intersect each other perpendicularly, the first incident surface being defined by an incident light on a boundary surface of the first reflecting member and a reflecting light from the boundary surface of the first reflecting member, and the second incident surface being defined by an incident light on a boundary surface of the second reflecting member and a reflecting light from the boundary surface of the second reflecting member, and
    wherein the third reflecting member and the fourth reflecting member are provided so that a third incident surface and a fourth incident surface intersect each other perpendicularly, the third incident surface being defined by an incident light on a boundary surface of the third reflecting member and a reflecting light from the boundary surface of the third reflecting member, and the fourth incident surface being defined by an incident light on a boundary surface of the fourth reflecting member and a reflecting light from the boundary surface of the fourth reflecting member.

2. The imaging apparatus according to claim 1, wherein the second reflecting member is of the same type as the first reflecting member and is arranged so as to correct the phase difference.

3. The imaging apparatus according to claim 1,
    wherein the third reflecting member is a first wavelength selecting member, and the fourth reflecting member is a second wavelength selecting member,
    wherein the second reflecting member is configured to reflect the reflected light in a direction intersecting a plane including an optical axis of the optical path in which the first reflecting member is provided, and the phase difference generated by a reflection of the first reflecting member is corrected by a reflection of the second reflecting member, and
    wherein the phase difference generated by a reflection of the measurement light from the first wavelength selecting member is corrected by the reflection of the measurement light from the second wavelength selecting member.

4. The imaging apparatus according to claim 1, further comprising:
    a polarization adjusting member provided on the optical path of the reference light downstream of the first reflecting member and the second reflecting member.

5. The imaging apparatus according to claim 1,
    wherein the third reflecting member is a first wavelength selecting member, and
    wherein the fourth reflecting member is a second wavelength selecting member, and
    wherein the phase difference generated by a reflection of the measurement light from the first wavelength selecting member is corrected by the reflection of the measurement light from the second wavelength selecting member.

6. The imaging apparatus according to claim 1,
    wherein the third reflecting member is a first scanning device configured to scan the measurement light,
    the fourth reflecting member is a second scanning device configured to scan the measurement light, and
    wherein the phase difference generated by a reflection of the measurement light from the first scanning device is corrected by a reflection of the measurement light from the second scanning device.

7. The imaging apparatus according to claim 1, further comprising:
    a fifth reflecting member provided on the optical path of the reference light so as to reflect and return the reference light towards the second reflecting member, wherein the fifth reflecting member is provided at a plane parallel to the first incident surface so that the reference light reflected by the fifth reflecting member returns to the boundary surface of the second reflecting member.

8. The imaging apparatus according to claim 7, wherein the second reflecting member is provided on the optical path of the reference light upstream of the first reflecting member in a direction of the reference light traveling to the fifth reflecting member.

9. The imaging apparatus according to claim 1, wherein a refractive index of the second reflecting member is the same as a refractive index of the first reflecting member so as to correct the phase difference.

10. An imaging apparatus configured to image an object to be examined, comprising:
 a light splitting unit configured to split light obtained by combining a returned light from the object to be examined irradiated with a measurement light and a reference light corresponding to the measurement light into a plurality of lights having different polarization components;
 a detecting unit configured to detect the plurality of lights;
 first reflecting members provided on an optical path of the measurement light and an optical path of the reference light;
 second reflecting members provided on the optical path of the measurement light and the optical path of the reference light and configured to correct a phase difference between different polarization components generated by the first reflecting members,
 wherein the first reflecting members and the second reflecting members are provided so that a first incident surface and a second incident surface intersect each other perpendicularly, the first incident surface being defined by an incident light on a boundary surface of the first reflecting members and a reflecting light from the boundary surface of the first reflecting members, and the second incident surface being defined by an incident light on a boundary surface of the second reflecting members and a reflecting light from the boundary surface of the second reflecting members.

\* \* \* \* \*